United States Patent [19]

Foxman

[11] 4,224,021
[45] Sep. 23, 1980

[54] ADJUSTABLE ATTACHMENT FOR A LABIAL ARCH RETAINER

[76] Inventor: David Foxman, Cedarbrook Hills, Apt. A-311, Wyncote, Pa. 19095

[21] Appl. No.: 931,029

[22] Filed: Aug. 4, 1978

Related U.S. Application Data

[63] Continuation-in-part of Ser. No. 760,334, Jan. 18, 1977, abandoned.

[51] Int. Cl.² ............................................... A61C 3/00
[52] U.S. Cl. .......................................... 433/2; 433/6; 433/18
[58] Field of Search ................... 32/14 B, 14 A, 14 E, 32/14 D; 433/2, 6, 18, 24

[56] References Cited

U.S. PATENT DOCUMENTS

| | | | |
|---|---|---|---|
| 737,881 | 4/1905 | Shelp | 32/14 A |
| 1,005,131 | 10/1911 | Angle et al. | 32/14 A |
| 1,166,766 | 1/1916 | Kelsey | 32/14 A |
| 1,227,073 | 5/1917 | Roach | 32/5 |
| 1,299,364 | 4/1919 | Lokey | 32/5 |
| 2,259,160 | 10/1941 | Glaser | 32/14 E |
| 2,674,040 | 11/1952 | Lenzer | 32/5 |
| 3,512,257 | 5/1970 | Stifter | 32/14 A |
| 3,987,547 | 10/1976 | Moss | 32/14 E |
| 4,059,900 | 11/1977 | Orthwein | 32/5 |

FOREIGN PATENT DOCUMENTS

| | | | |
|---|---|---|---|
| 780623 | 4/1935 | France | 32/5 |
| 371930 | 4/1973 | U.S.S.R. | 32/14 B |

OTHER PUBLICATIONS

"T-LAR", brochure.
"Better Orthodontia", ad, Dental Survey, Jun. 1935, p. 102.
"Occlus-O-Guide", information booklet, 1975.

Primary Examiner—Louis G. Mancene
Assistant Examiner—John J. Wilson
Attorney, Agent, or Firm—Weiser, Stapler & Spivak

[57] ABSTRACT

An improved adjustable attachment for a labial arch retainer. The retainer is of the type having a palatal section configured to conform to the roof of the mouth of a patient, a pair of extension wires extending anteriorly from the palatal section, an attachment hook provided at the terminal end of each extension wire, and a resilient synthetic band adapted to exert pressure against the teeth of the patient. The adjustable attachment is connected between the resilient band and the attachment hook in a manner which permits the length of the resilient band to be varied thereby permitting adjustment of the pressure exerted against the teeth of the patient.

10 Claims, 3 Drawing Figures

ADJUSTABLE ATTACHMENT FOR A LABIAL ARCH RETAINER

This application is a continuation-in-part of my co-pending application Ser. No. 760,334, filed Jan. 18, 1977, abandoned Jan. 7, 1979.

BACKGROUND OF THE INVENTION

This invention relates generally to the field of orthodontic retainers, and in particular to an improved adjustable attachment for use in conjunction with such retainers.

In my application Ser. No. 760,334, a retainer is disclosed which comprises a palatal section molded to follow the configuration of the mouth of a patient, tooth engaging means adapted to engage the anterior surfaces of the first or second molars to hold the palatal section in place, a resilient band adapted to exert pressure against the teeth, and a band securing means to secure the resilient band to the palatal section.

In designing an orthodontic device, easy adjustment of the pressure exerted against the teeth of the patient is an important parameter for obtaining proper realignment of the teeth. The retainer disclosed in application Ser. No. 760,334 provides two alternative embodiments of an attachment means capable of use for this purpose. Although the two embodiments shown are well suited to the performance of a wide variety of orthodontic treatments, it has been determined that in certain situations use of a more permanent attachment means would be preferable, for example, in situations where the patient is a young child or otherwise uncooperative during the treatment process. Additionally, the prior device has proved somewhat difficult or costly in manufacture.

Prior workers in the art have recognized the need for such an adjustable attachment and have devised various attachments which are particularly suited for such a purpose. For example, U.S. Pat. No. 787,861 discloses a threaded, adjustable attachment means using a nut which presses against a bearing block. Such an apparatus may easily be tampered with by the patient and also has the disadvantage of requiring the placement of protruding structure in the mouth of the patient. U.S. Pat. No. 3,512,257 discloses an orthodontic device which utilizes hooks variably placed in holes provided as part of a head strap to permit adjustment of the pressure exerted against the teeth of the patient. Such an apparatus easily permits an uncooperative patient to change the adjustment of the device. In fact, even a cooperative patient may forget into which holes the hooks must be placed, hampering uniform and proper treatment.

It would therefore often be advantageous to utilize a more permanent, yet adjustable, attachment means in connection with orthodontic treatment.

SUMMARY OF THE INVENTION

This invention relates generally to the field of orthodontic retainers, and in particular to an improved adjustable attachment which permits the secure and simple adjustment of the pressure exerted against the teeth of a patient by the resilient band which is a part of the retainer.

Orthodontic retainers generally comprise a palatal section which is molded to conform to the roof of the mouth of a patient, a means for properly positioning the palatal section in the mouth of the user, and a strap or band connected to the palatal section and adapted to apply pressure against the teeth of the patient. The pressure exerted by the strap or band may be made adjustable by placing an adjustment means between that strap or band and the palatal section.

In accordance with the present invention, an attachment means is provided which permits the secure and simple adjustment of the pressure required for proper treatment. This is accomplished by providing an adjustable attachment which is permanently connectable to the strap or band and which is adjustably connectable to wires extending anterially from the palatal section to the strap or band. The anterially extending wires are inserted into tubular connectors which are part of the adjustable attachment and then bent over the top of the tubular connectors slightly to provide the secure attachment of components desired. Readjustment is easily accomplished by an orthodontist by straightening the end of the wire, changing the tubular connector into which the wire is inserted and again bending the wire over at its end.

It is therefore an object of the present invention to provide a novel adjustable attachment for use in connection with a labial arch retainer which permits adjustment of the pressure exerted against the teeth of a patient.

It is another object of the present invention to provide a novel adjustable attachment for use in connection with a labial arch retainer which permits the simple adjustment of pressure exerted against the teeth of a patient while assuring a secure interconnection of components of the retainer.

It is another object of the present invention to provide a novel adjustable attachment for use in connection with a labial arch retainer which resists tampering by the patient.

It is another object of the present invention to provide a novel adjustable attachment for a labial area retainer which is readily adapted to the existing components of the retainer, requiring a minimum amount of modification or reformation during use.

It is another object of the present invention to provide a novel adjustable attachment for a labial arch retainer which is simple in design, inexpensive of manufacture and easy to use.

These and other objects will become apparent to those skilled in the art from the following disclosure of the preferred embodiment of the invention taken in conjunction with the drawings provided in which like reference characters refer to similar parts throughout the several views provided in which:

DESCRIPTION OF THE PREFERRED EMBODIMENT OF THE INVENTION

Figure 1:
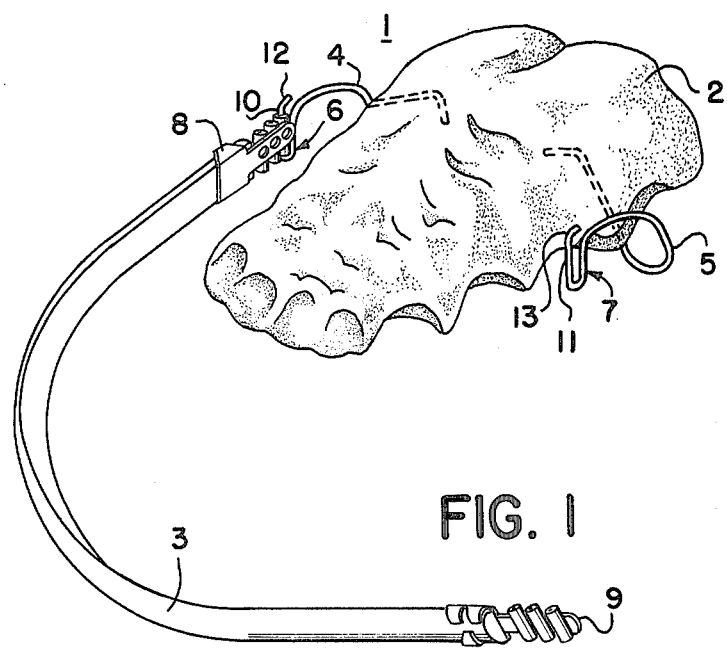
FIG. 1 is a perspective view of the members of a labial arch retainer also showing the interconnection between the adjustable attachment and the remaining members of the retainer.

Although specific terms are used in the following description for the sake of clarity, these terms are intended to refer only to the particular structure of the invention selected for illustration in the drawings, and are not intended to define or limit the scope of the invention.

Referring now to the drawings, there is shown in FIG. 1 a labial arch retainer 1 which is suitable for use in closing and retaining the spacing between the teeth of a user or patient (not shown). The retainer 1 illustrated comprises a palatal section 2, a resilient synthetic band 3, and a pair of extension wires 4, 5. The extension wires 4, 5 anterially extend from the palatal section 2 and serve as a means for engaging the teeth of the patient. Each extension wire 4, 5 is provided with a means for attaching the resilient band 3 to the end of the extension wires 4, 5, such as the attachment hooks, 6, 7. A pair of adjustable attachments such as the band connectors 8, 9 connect to the opposite ends of the resilient band 3 to permit easily adjustable connection to the extension wires 4, 5.

The palatal section 2 is manufactured of plastic or other suitable material which is molded, cast or otherwise conventionally formed to closely conform to the configuration of the roof of the mouth of the user or patient. The techniques for molding such a structure are well known in the art.

The extension wires 4, 5 are embedded in and extend anterially from the palatal section 2 to provide convenient engagement for the ends of the resilient band 3. These extension wires 4, 5 are embedded in the palatal section 2 during formation of the palatal section 2 to provide proper support to the extension wires 4, 5.

The resilient band 3 is designed to exert continuous closing force anterially of the user's teeth to provide the realignment of the teeth desired. The resilient band 3 may be formed of any suitable, resilient plastic material such as polyethylene or polypropylene plastic. For cosmetic purposes the band material is preferably transparent to permit the teeth of the user to be visible therethrough. The resilient band 3 should be of a size which is comfortable in the mouth of the user or patient, preferably having a width of approximately 3 mm and a thickness of approximately 1 mm. As stated in the copending application, the band preferably is substantially hemispherical or semi-elliptical in cross section.

Each extension wire 4, 5 is provided with an attachment hook 6, 7 which is particularly adapted for use in connection with the band connectors 8, 9. Each attachment hook 6, 7 is generally U-shaped in configuration and extends upwardly from the end of the attachment wire 4, 5 in a linear segment 10, 11. Sufficient length should be provided in forming the linear segments 10, 11 to assure that sufficient wire remains after insertion of the band connectors 8, 9 to form a hooked end 12, 13, the purpose of which will be more fully described below.

An adjustable band connector 8, 9 is preferably provided at each end of the resilient band 3 to provide a maximum adjustable differential in length. This is preferable to permit proper adjustment of the pressure exerted against the teeth of the patient in a manner to be described below. However, it is also possible to place such an adjustable attachment means at only one end of the resilient band 3, the other end having a fixed attachment means, should a smaller degree of adjustment be required.

Figure 2:
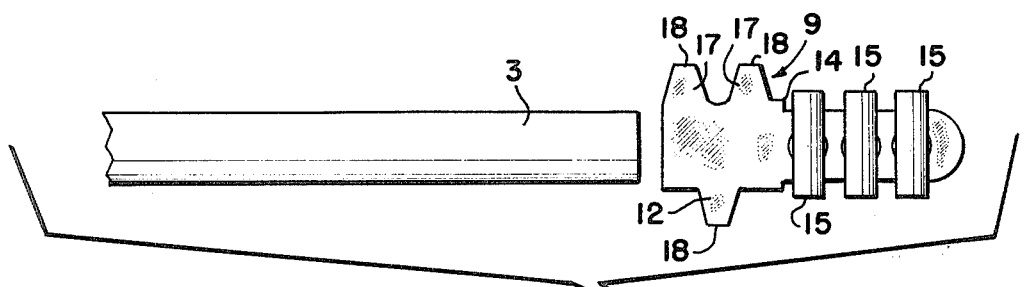
FIG. 2 is an enlarged, partial, exploded view of the adjustable attachment prior to its connection to the resilient band of the retainer.

The band connector 8, 9, which is more clearly illustrated in FIG. 2, comprises a flat blank 14 and one or more hollow, spaced, tubular sections 15 which serve as a means for adjustably engaging attachment hooks 6, 7. Both the blank 14 and tubular sections 15 may be cut to size from any standard metal stock conventionally used for orthodonture, for example stainless steel.

Figure 3:
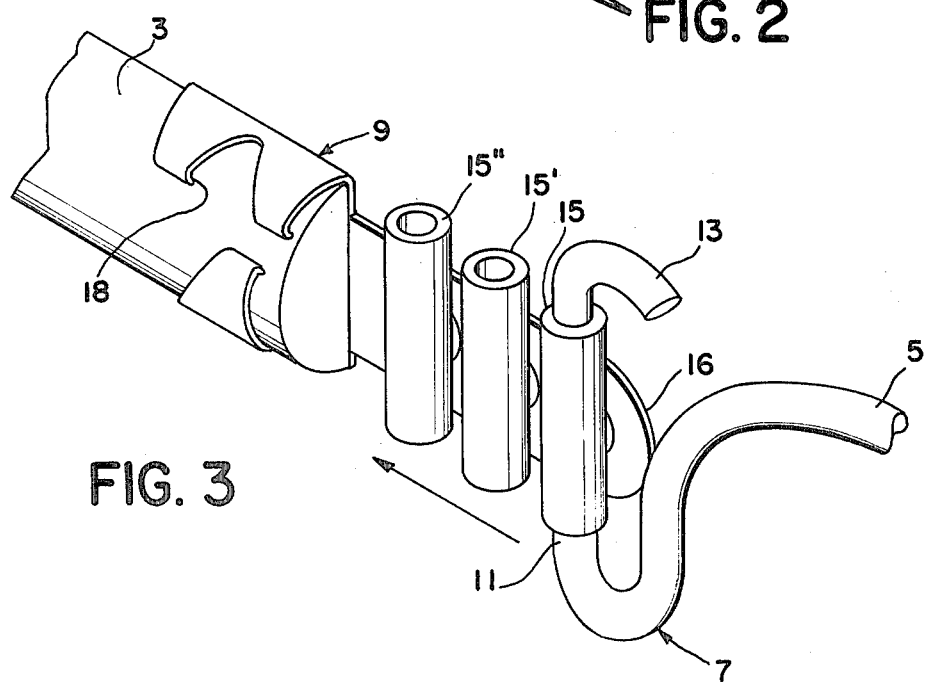
FIG. 3 is an enlarged, partial, isometric view of the adjustable attachment as it would appear when in use.

The blank 14 is provided with a longitudinal extension 16 to which may be securely attached the tubular sections 15, and a plurality of oppositely facing fingers 17 which serve as a means for connecting the resilient band 3 to the blank 14. The fingers 17 may be used to crimp the band connector 8, 9 to the resilient band 3 by appropriately bending the fingers 17 around that resilient band 3. As illustrated in FIG. 3, the tips 18 of the fingers 17 may be curved inwardly toward the resilient band 3 to bite into the band 3 and provide additional strength to the crimped combination. It is also possible to embed the end of the band connector 8, 9 in the end of the resilient band 3 during formation of the latter component. However, crimping is preferable.

The hollow tubular sections 15 may be cut to any size appropriate for a given application. The tubular sections 15 can be attached to the longitudinal extension 16 using any of several known methods, for example spot welding. The tubular sections 15 are ordinarily placed at approximately a ninety degree angle from the axis defined by the longitudinal extension 16 and the resilient band 3. This provides uniform adjustment and longitudinal forces along the entire width of the resilient band 3. However, the tubular sections 15 could also be placed at other angles including zero degrees to the extension 16 if desired for a particular application. The linear segments 10, 11 are formed at an angle complementary to that of the tubular sections 15 to facilitate their interconnection.

FIG. 3 illustrates in greater detail the preferred manner in which the band connector 9 is connected to the remaining elements of the retainer 1. The band connector 9 is connected at one end to the resilient band 3 by crimping the flat blank 14 to the resilient band 3. As previously mentioned, the band connector 9 could also be embedded into the resilient band 3 during formation of the latter structure. In either case, the linear segment 11 of the attachment hook 7 is fitted into a selected hollow tubular section 15. Thereafter, the upper end 13 of the linear segment 11 is bent and hooked over to assure a safe and secure closure of the assembly.

The amount of pressure exerted against the teeth (not shown) of the user or patient is directly proportional to the elasticity of the resilient band 3 and the distance between the attachment hooks 6, 7. Therefore the pressure exerted depends directly upon which of the several tubular sections 15 are used to engage the linear segments 10, 11. The force exerted would generally increase as the linear segment 11 is moved to successive tubular members 15 in the direction of the arrow shown in FIG. 3. Variation of this force may be accomplished by varying the position of either or both of the band connectors 8, 9.

As the teeth are moved from the forces exerted upon them, it will be necessary to periodically adjust the length of the resilient band 3 to accommodate these changes. This may be readily accomplished by straightening the hooked end 13, disengaging the tubular section 15 from the linear segment 11, engaging a second tubular section such as 15' or 15" over the linear segment 11, and re-bending the hooked end 13 to retain the assembly in place. In this manner, the force exerted upon the teeth may be quickly varied yet securely maintained whenever necessary to assure the proper realignment of the teeth of the user or patient.

It may therefore be seen that the above disclosed invention serves well to accomplish the object previously stated. It may also be seen that the above-described invention may be embodied in other specific forms in addition to those above disclosed and therefore the disclosure made should be interpreted in an illustrative and not a limiting sense.

What is claimed is:

1. In a labial arch retainer of the type having a palatal section configured to closely conform to the roof of the mouth of a user, tooth engaging means extending from the palatal section to maintain the retainer in place, band attachment means provided in the tooth engaging means, and a resilient band connectable to the band attachment means to apply retention forces upon the teeth of the user, an improved band connector which comprises a central body having means for connecting the body to the resilient band and a longitudinal extension having a plurality of spaced means for engaging the band attachment means, wherein the band attachment means is adapted to adjustably lock the band to the band attachment means.

2. The retainer of claim 1 wherein the means for connecting is adapted to be crimped onto the resilient band.

3. The retainer of claim 2 wherein the means for connecting has a plurality of fingers extending outwardly from the body, the fingers being adapted to bend over the resilient band to thereby affix the means for connecting to the resilient band.

4. The retainer of claim 1 wherein the means for connecting is adapted to be embedded in the resilient band.

5. The retainer of claim 1 wherein spaced means for engaging the band attachment means each comprise a hollow, tubular section connected to the longitudinal extension of the body.

6. The retainer of claim 5 wherein the hollow tubular sections and the longitudinal extension are connected to each other at substantially a ninety degree angle.

7. The retainer of claim 6 wherein the band attachment means comprises a linear segment attached to the end of the tooth engaging means.

8. The retainer of claim 7 wherein the linear segment is formed at an angle complementary to that of the hollow, tubular section.

9. The retainer of claim 7 wherein the terminal end of the linear segment is adapted to be bent over one of said hollow tubular sections after it is placed over the linear segment, whereby the band attachment means is locked to the body to affix the resilient band in place.

10. The retainer of claim 5 wherein the spaced means for engaging the band attachment means comprises a plurality of hollow, tubular sections connected to the longitudinal extension of the body in longitudinal, spaced relationship whereby band tension adjustment may be easily accomplished by connecting the band attachment means to different sections of said hollow, tubular sections.

* * * * *